United States Patent
Church et al.

(10) Patent No.: US 7,387,876 B2
(45) Date of Patent: Jun. 17, 2008

(54) AMPLIFICATION OF TRACE AMOUNTS OF NUCLEIC ACIDS

(75) Inventors: George M. Church, Brookline, MA (US); Kun Zhang, Brighton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 9 days.

(21) Appl. No.: 11/066,559

(22) Filed: Feb. 28, 2005

(65) Prior Publication Data

US 2006/0014167 A1  Jan. 19, 2006

Related U.S. Application Data

(60) Provisional application No. 60/548,634, filed on Feb. 27, 2004.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search .................. None
See application file for complete search history.

(56) References Cited

U.S. PATENT DOCUMENTS 5,162,209 A * 11/1992 Scheele .................. 435/91.41
5,487,985 A * 1/1996 McClelland et al. ....... 435/91.2
5,814,444 A * 9/1998 Rabinovitch ................. 435/6

FOREIGN PATENT DOCUMENTS

WO  WO 98/49345  * 11/1998
WO  WO 03/087402  * 10/2003

OTHER PUBLICATIONS

Sorensen, K.J., Anal. Biochem., vol. 324, pp. 312-314 (Jan. 2004).*
Nilsson, M. et al., Nucl. Acids Res., vol. 30, e66 (p. 1-7) (2002).*
Dean, Frank B. et al., "Comprehensive human genome amplification using multiple displacement amplification," *PNAS*, Apr. 16, 2002, vol. 99, No. 8, pp. 5261-5266.
"Locked Nucleic Acid," http://www.qualitysystems.com.tw/Proligo/LNA.htm.
Zhang, Kun et al., "Genome sequencing from single cells with ploning," 2005 Geonomics: GTL Workshop, Feb. 6-9, 2005, (Poster and Abstract).

* cited by examiner

*Primary Examiner*—Teresa E. Strzelecka
(74) *Attorney, Agent, or Firm*—Banner & Witcoff, Ltd.

(57) ABSTRACT

Methods of reducing background during amplification of small amounts of nucleic acids employ careful analysis of sources of low level contamination. Ultraviolet light can be used to reduce nucleic acid contaminants in reagents and equipment. "Primer-dimer" background can be reduced by judicious design of primers. We have shown clean signal-to-noise with as little as starting material as one single human cell (~6 picogram), *E. coli* cell (~5 femtogram) or *Prochlorococcus* cell (~3 femtogram).

42 Claims, 6 Drawing Sheets

Phylogenetic tree of 9312 clade based on the ITS sequence. Entries in green are known isolates. Entries in black are plones from HOT.

US 7,387,876 B2

AMPLIFICATION OF TRACE AMOUNTS OF NUCLEIC ACIDS

CROSS REFERENCE

This application claims the benefit of provisional application Ser. No. 60/548,634, filed Feb. 27, 2004, the disclosure of which is expressly incorporated herein.

STATEMENT OF GOVERNMENT INTERESTS

This invention was made with Government support under Grant Number DE-FG02-02ER63445 awarded by the Department of Energy. The Government has certain rights in the invention.

FIELD OF THE INVENTION

The present invention relates to methods of amplifying DNA or RNA when only small amounts are available as well as methods of cloning single molecules.

BACKGROUND OF THE INVENTION

At nucleic acid amount less than a nanogram, various "whole genome amplification" (WGA) strategies, such as multiple displacement amplification (MDA) (Dean et al. (2002) *Proc. Natl. Acad. Sci. U.S.A.* 99:5261-5266, incorporated herein by reference) yield a "background" of undesired amplification products. The ability to efficiently amplify trace amounts of nucleic acids with a minimum of undesired background is highly desirable in research and diagnostic methods, including, but not limited to, clinical, food, environmental and forensic investigative testing.

SUMMARY OF THE INVENTION

In a first embodiment of the invention a method of nucleic acid amplification is provided. A sample of polymerase is exposed to ultraviolet light for a sufficient time to reduce nucleic acid contamination of said polymerase and to produce an exposed sample of polymerase. A reaction mixture comprising a nucleic acid template is amplified using the exposed sample of polymerase.

In a second embodiment of the invention a method of nucleic acid amplification is provided. A nucleic acid template is amplified in a reaction mixture. The reaction mixture comprises one or more restricted-randomized oligonucleotide primers. Restricted-randomized primers do not comprise random hexamers ($N_6$, wherein N=A, C, G, or T). The reaction mixture also comprises a template-dependent polymerase, and mononucleotide triphosphates. The amplification is performed under conditions permitting hybridization of the primers to the template.

In a third embodiment of the invention a method for amplifying a genome from a single cell is provided. A genome from a single cell is amplified using a random hexamer primer ($N_6$) and a polymerase in a real-time amplification reaction. The polymerase in the reaction is contaminated with less nucleic acid than 1/100 (w/w) of the genome in the reaction.

In a fourth embodiment of the invention a method is provided for amplifying a genome from a single cell. A genome from a single cell is amplified using a restricted-randomized primer ($D_6$) and a polymerase in a real-time amplification reaction. The polymerase in the reaction is contaminated with less nucleic acid than 1/100 (w/w) of the genome in the reaction.

The present invention addresses the need to reduce background during amplification of small amounts of nucleic acids. Accordingly, the present invention reduces nucleic acid contaminants as a background source using ultraviolet (UV) light to inactivate the nucleic acid contaminants without inactivating reagents (e.g., polymerases). The present invention also reduces "primer-dimer" background sources using restricted-randomized primers.

BRIEF DESCRIPTION OF THE DRAWINGS

FIGS. 1A-1D. Isothermal amplification based on the multiple displacement process is an exponential amplification, and can be used as an ultra-sensitive DNA quantification method.

FIGS. 2A-2E. Confirmation of single-cell whole genome amplification with strain-specific PCR and Affymetrix *E. coli* Antisense genomic chip™ hybridization.

FIGS. 3A-3B.

FIGS. 4A-4B. Phylogenetic Analysis of plones.

DETAILED DESCRIPTION

The present invention provides methods for reducing two sources of background during amplification of small amounts of nucleic acids: the presence of nucleic acid contaminants in equipment and reagents, including polymerase preparations, and the generation of polymers ("primer-dimers") from nucleic acid primers. In one embodiment, a method of reducing nucleic acid contamination using UV light to inactivate nucleic acid contaminants without inactivating reagents necessary for amplification (e.g., polymerases) is provided. In another embodiment, a method of reducing primer-dimer background sources using restricted-randomized primers is provided.

As used herein, restricted-randomized primers are randomized primers that do not include all four of the physiological nucleotides (A, C, G, T/U) and include, but are not limited to oligonucleotide mixes (discussed further below), peptide nucleic acid (PNA) components (see Lutz et al. (1999) *Nucleosides Nucleotides* 18:393), locked nucleic acid (LNA) components (available from Quality Systems, Inc., Taipei, Taiwan) and the like. The PNA and/or LNA components can stabilize heteroduplexes between short primers and template DNA, allowing more efficient priming on double-stranded DNA. At low levels of template DNA, totally random primers can hybridize to each other rather than to true target template and generate spurious amplification products. By using restricted-randomized primers which have restricted nucleotide base content primer-primer hybridization can be diminished and with it spurious amplification products. The restricted-randomized primers may contain:

$B_6$ (wherein B=not A=C+G+T),
$D_6$ (wherein D=not C=A+G+T),
$H_6$ (wherein H=not G=A+C+T),
$V_6$ (wherein V=not T=A+G+C),
$M_6$ (wherein M=A+C),
$W_6$ (wherein W=A+T),
$Y_6$ (wherein Y=T+C),
$R_6$ (wherein R=A+G),
$K_6$ (wherein K=G+T/U),
$I_3D_4$ (wherein I=inosine, and wherein D=not C),
$I_2M_7$, (wherein I=inosine and M=A+C),
$M_7$. (wherein M=A+C), or combinations thereof.

Restricted-randomized primers do not include $N_6$, $N_7$, $N_8$, or $N_n$, wherein N=A+C+G+T), i.e., primers in which all four nucleotides are included.

The amount of UV treatment necessary will vary depending on the level of contamination in a particlar polymerase preparation and the use to which the polymerase will be put. If the polymerase preparation is heavily contaminated, then more treatment will be necessary. If the polymerase will be used to amplify a single, small genome, then more treatment will be necessary than for amplifying a larger genome or than for amplifying more copies of a smaller genome. Thus, bacterial genomes typically require purer polymerase preparations than mammalian genomes for single cell or single genome sequencing. Similarly, single chromosome sequencing requires purer preparations than sequencing of all chromosomes of a multi-chromosomal cell or organism. Viral and bacteriophage genomes are typically even smaller and require the use of exceedingly pure preparations of polymerase. Testing to determine the amount of treatment necessary can be accomplished using isothermal amplification with restricted-randomized primers. As discussed below, the amount of contaminating nucleic acids can be calculated by observing compression of amplification kinetics curves of dilutions of known amounts of nucleic acid. Empirical testing has determined that $R_6$ and $M_6$ provide excellent results for this purpose.

We have performed proof-of-principle experiments on *E. coli*. However, one major goal for single cell genome sequencing is to sequence organisms of totally unknown genome sequence that are difficult to culture. In these cases, because one might accidentally take the amplicons that are generated by primer-primer interaction as the genomic sequence of a new organism, it is essential that a no-template control be included in any single cell amplification experiment to monitor the level of background amplification. Moreover, the t50 of the no-template control must be much larger than that of the single cell. If the approximate size of the target genome is known, a side-by-side experiment with a DNA dilution series is recommended, in order to verify that the level of initial contaminating DNA is at least 100-fold below the mass of a single target genome.

This invention is further illustrated by the following examples, which should not be construed as limiting. The contents of all references, patents and published patent applications cited throughout this application are hereby incorporated by reference in their entirety for all purposes.

EXAMPLE 1

Reduction of Background Noise

To reduce primer-dimer background sources, restricted-randomizeds to the conventional random primers ($N_6$) were used such as, for example, $B_6$ (wherein B=not A=C+G+T), $D_6$ (wherein D=not C), $H_6$ (wherein H=not G), $V_6$ (wherein V=not T), $M_6$ (wherein M=A+C), $W_6$ (wherein W=A+T), $Y_6$ (wherein Y=T+C), $I_3D_4$ (wherein I=inosine), $I_2M_7$, $M_7$ and the like. These mixes of restricted-randomized oligonucleotide primers have the advantages of lower complexity than $N_6$ (e.g., $B_6$=729 combinations of nucleotides, $M_6$=64 combinations of nucleotides, $D_4I_3$=81 combinations of nucleotides, vs. $N_6$=4096 combinations of nucleotides), fewer self-complementary pairs and similar or higher annealing stability. For example, without intending to be bound by theory, $M_6$ should have few, if any, self-matches since there is zero chance for G-C, A-T, or G-T base pairs (note that inosine pairs to some extent with C, T, and A). $M_6$, $H_6$, $W_6$, $Y_6$, $M_5$, $M_7$, and the like also are desireable, in that they are compatible with bisulfite-treated DNA. Clean signal-to-noise ratios were obtained using as little starting material one single *E. coli* cell (~5 femtograms) using a UV-treated polymerase and D6 primer, when the background is properly controlled using the real-time amplification system. Other primer pools mentioned above were also used to generate amplified products with clean signal-to-noise ratios.

EXAMPLE 2

Currently genome sequencing is performed on cell populations because of the difficulty in preparing sequencing template from single cells. This makes the genome sequences of many difficult-to-culture organisms inaccessible or poorly assembled. We have developed a method that enables genome sequencing from a single cell by performing polymerase cloning (ploning). In this method, we prepare sequencing templates from single cells with real-time multiple displacement amplification (rtMDA), which allows us to tackle the big technical challenge in single-cell whole genome analysis: to detect and suppress spurious amplification while targeting a single molecule of a microbial chromosome.

Experiments on *Escherichia coli* show that, (1) an amplification magnitude of $10^9$ was achieved by rtMDA, (2) strain-specific genetic signatures were preserved, (3) neither spurious amplification product nor chimeric sequence was detected, (4) an estimated 97% of the target genome could be recovered from a polymerase clone (plone) at the 10× sequencing depth. The remaining regions are not missing, but present at lower copy numbers, and are easily recovered by PCR. Since the low-coverage regions seem random, genome coverage can be improved by pooling the sequencing reads from two or more plones of the same type of cells during the assembly stage. Furthermore, we successfully performed ploning on both fresh and frozen *Prochlorococcus* cells, and obtained nearly complete coverage on both strains (MED4 and MIT9312) we tested. Plones of single cells from an ocean sample (from the Hawaii Ocean Time-series) are being screened for *Prochlorococcus* cells for genome sequencing. Initial results indicate successful amplification of single *Prochlorococcus* cells from this sample. After further screening of genome coverage, whole genome shot-gun sequencing can be performed on a few selected plones.

EXAMPLE 3

Ocean photosynthetic microbes are dominated by *Prochlorococcus*. The genome sequences of three lab strains (MED4, MIT9313, MIT9312) have been studied in great extent. Yet the genome diversity in uncultured ocean samples remains unclear. To address this question, plones of single cells were prepared from the Hawaii Ocean Time-series and further characterized in this study.

Materials and Methods

Ultra-low background real-time isothermal amplification. Lab or field samples were diluted to or below single-cell level, then treated with lysozyme prior to amplification. We performed isothermal amplifications essentially as described by Dean et al. (Dean et al. 2002, *Proc. Natl. Acad. Sci. U.S.A.* 99:5261-5266), except that SYBR Green I was added to the reaction to a final concentration of 0.1×, and the reactions were carried out in a real-time PCR thermocycler at 30° C. A strict sample handling and experimental procedure was followed, which is essential to achieve sub-femtogram levels of background.

Affymetrix *E. coli* chip™ hybridization and analysis. We purified single cell amplicons with Microcon YM30 columns, performed labeling and hybridization following the Affymetrix standard protocol. Data analyses was primarily conducted with the Bioconductor Affymetrix package with a customized probe set package, in which probes was grouped into non-overlapping 2 kb bins along the chromosome.

Shotgun cloning, sequencing and sequence analyses. We performed shotgun cloning of single cell amplicons using the TOPO Shotgun cloning kit (Invitrogen, CA), DNA sequencing was performed by the Biopolymers Facility (Harvard Medical School).

Freezing and preserving of whole cells. We tested a number of protocols to freeze and preserve intact cells of *Prochlorococcus* in order to facilitate field sampling. We tested DMSO, paraformaldehyde, glycerol and gluteraldehyde as freezing agents prior to ploning. Random PCR primers targeting the genome of *Prochlorococcus* isolates were used to assess coverage of ploning on frozen cells.

Results

Figure 1:
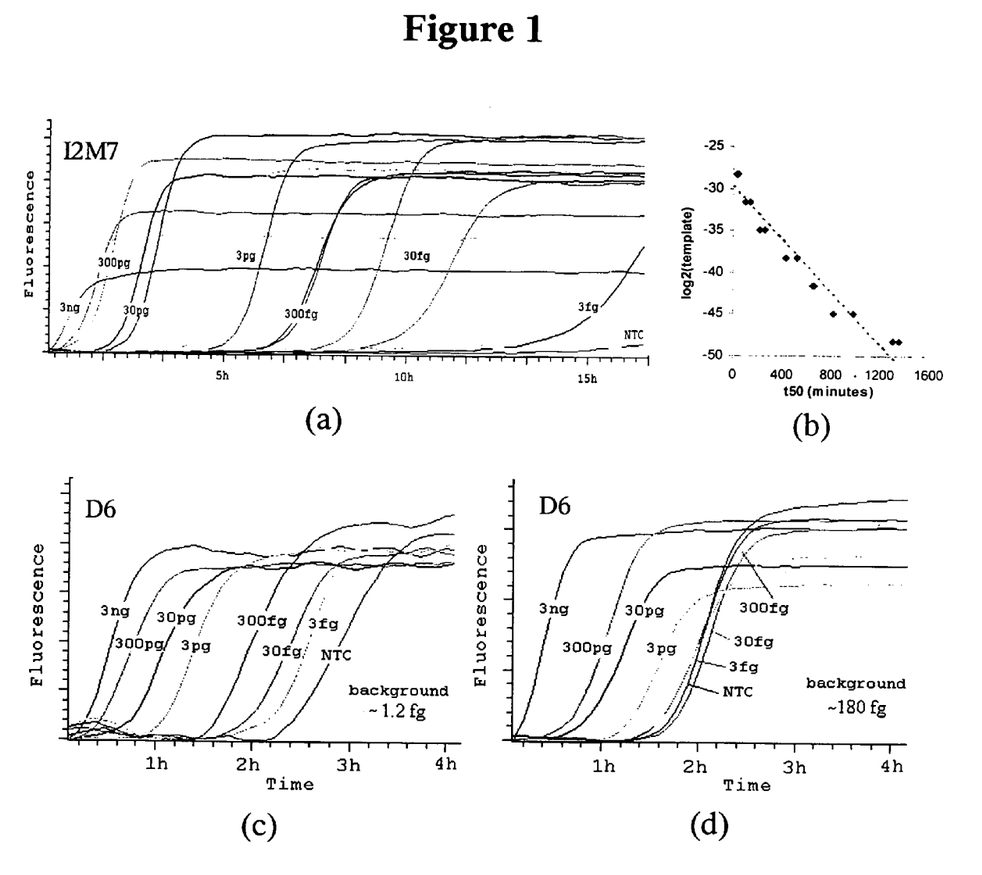
(FIG. 1A) Amplification curves for duplicated 10-fold dilution series of human genomic DNA as well as two no-template controls. The time amplification reaches an exponential growth stage depends on the amount of template DNA.
(FIG. 1B) The time an amplification reach 50% of its saturation level (t50) and the amount of template DNA has a good log-linear fit.
(FIG. 1C) When the level of background amplification is low, amplification curves for the 10-fold dilution series are well separated. The doubling time and the level of background contamination can be calculated based on the logistical regression on template amounts and t50 values.
(FIG. 1D) The amplification curves at the low end are compressed in the presence of a high level of background, which was probably due to DNA contamination in water. The y-axes are in arbitrary fluorescent unit. The fluorescent signals between different experiments are not comparable.
Figure 2:
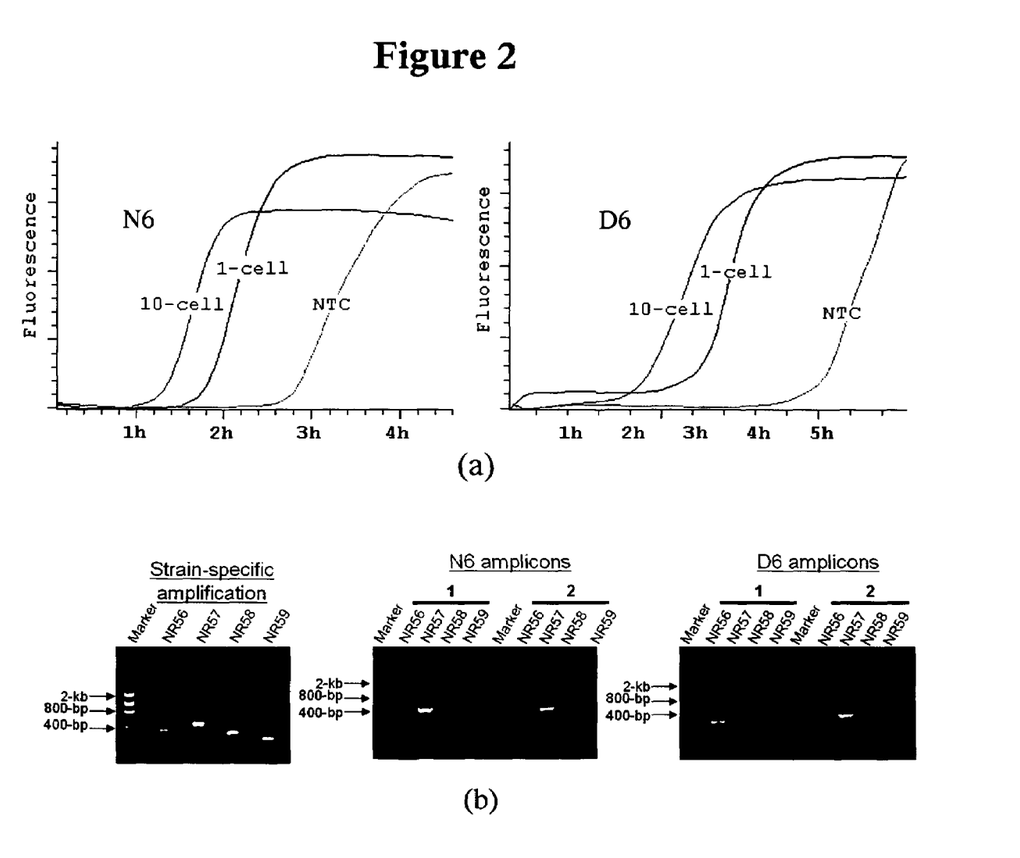
(FIG. 2A) Real-time isothermal amplification from single cells were performed when the background amplifications were suppressed below the mass of a single *E. coli* genome.
(FIG. 2B) The four *E. coli* strains used in this experiment can be identified by strain-specific PCR, which generates PCR products with unique size (left panel). The four single cell amplicons were confirmed by strain-specific PCR, indicating the two N6 amplicons and one D6 amplicon were from the NR57 strain, while the other D6 amplicon was from the NR56 strain.
(FIG. 2C) The deletion at bio locus leads to a sharp drop of EcNR1/MG1655 ratio (left panel), which is accurately preserved in three single cell amplicons. The pattern is less obvious for the first D6 amplicon because the right flanking region is underrepresented as well.
(FIG. 2D) The three amplicons from the NR57 strain also capture the strain-specific deletion at the proBA locus.
(FIG. 2E) The amplicon from the NR56 strain (D6 amplicon #1) has a small drop of hybridization intensity ratio at the glyA locus. The pattern of deletion is less clear because the neighboring region is underrepresented in this amplicon too.

Real-time ultra-low background isothermal amplification. We monitor the dynamics of isothermal amplification in real time with SYBR Green I (Hafner, et al. 2001. Isothermal amplification and multimerization of DNA by Bst DNA polymerase. *Biotechniques* 30: 852-856.). We found that MDA, like rolling-circle amplification (Lizardi et al., 1998, Mutation detection and single-molecule counting using isothermal rolling-circle amplification. *Nat Genet* 19: 225-232, incorporated herein by reference), has an exponential growth stage, and that the time it takes for an amplification to reach its 50% of saturated level (t50) is a good summary statistic to capture the underlying amplification dynamics: there is a log-linear relationship between t50 and the amount of DNA templates (FIG. 1a, 1b), thus providing a way to estimate background levels. We developed an amplification system with zero endogenous background based on a partially degenerate primer, R6 (a random hexameric sequence of A and G), because there is no base-pairing potential between any two primer molecules. Based on this system, we were able to systematically investigate the sources of exogenous contamination, and suppress the background amplification to a level that is at least 100-fold lower than the mass of target genome (FIG. 2a).

Amplification from single *E. coli* cells. A mixture of four *E. coli* strains were diluted to the single-cell level, and amplified using the real-time ultra-low background isothermal amplification we established. Assuming a Poisson distribution, for any amplicon (called plone) that is tested positive on only one strain-specific marker, there is an 88% chance that it was amplified from a single cell. We selected two plones from single cells (FIG. 2b) for hybridization to Affymetrix *E. coli* genomic chips™. We found that the amplification led to bias in copy number along the chromosome (FIG. 2c), and the bias is not locus-specific (FIG. 2d,2e). By calibrating the hybridization intensities with absolute copy number determined by real-time PCR at eight loci, we estimated the genome coverage at different sequencing depth (Table 1).

TABLE 1

Genome coverage of single cell amplicons.

| Sequencing depth | N6 amplicons | | |
|---|---|---|---|
| | #1 | #2 | Combined |
| 1X | 39.26% | 52.08% | 43.16% |
| 2X | 70.19% | 77.77% | 83.46% |
| 4X | 87.58% | 89.33% | 96.95% |
| 10X | 96.64% | 97.00% | 99.91% |
| 20X | 98.39% | 98.88% | 100.00% |
| 50X | 99.78% | 99.69% | 100.00% |

Because of the amplification bias, one needs a 10× sequencing depth to achieve 97% coverage of the genome. However, if the sequences of two plones are combined, the sequencing depth could be reduced to 4×. We carried out unbiased sampling of the sequences in one plone and a no-template control by shot-gun cloning and sequencing. All sequences from the plone were mapped uniquely to the *E. coli* genome, and no spurious sequence was found. Four mosaic sequences were identified, and further experiments show that they were due to the shot-gun library construction rather than amplification.

Figure 3:
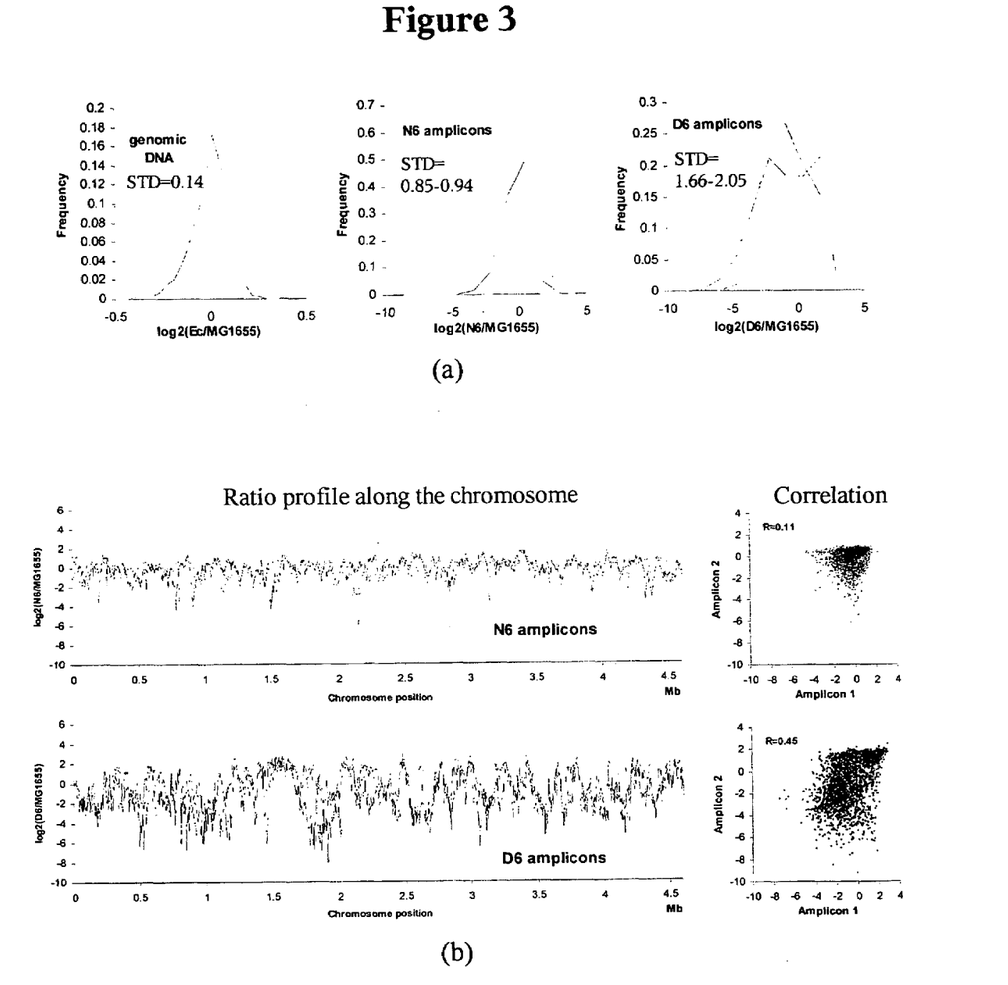
(FIG. 3A) Comparison of variation of normalized hybridization intensities (shown as log2-transformed ratios) among genomic DNA, N6 amplicons and D6 amplificons. D6 amplicons have approximately twice amount of variation compared with the N6 amplicons, which again have a 6.5-fold increase in variation compared with genomic DNA.
(FIG. 3B) The ratio profiles along the *E. coli* chromosome and the correlations between independent experiments. The N6 amplicons are in the top panel and the D6 amplicons are in the bottom panel. R is correlation coefficient.
Figure 4A:
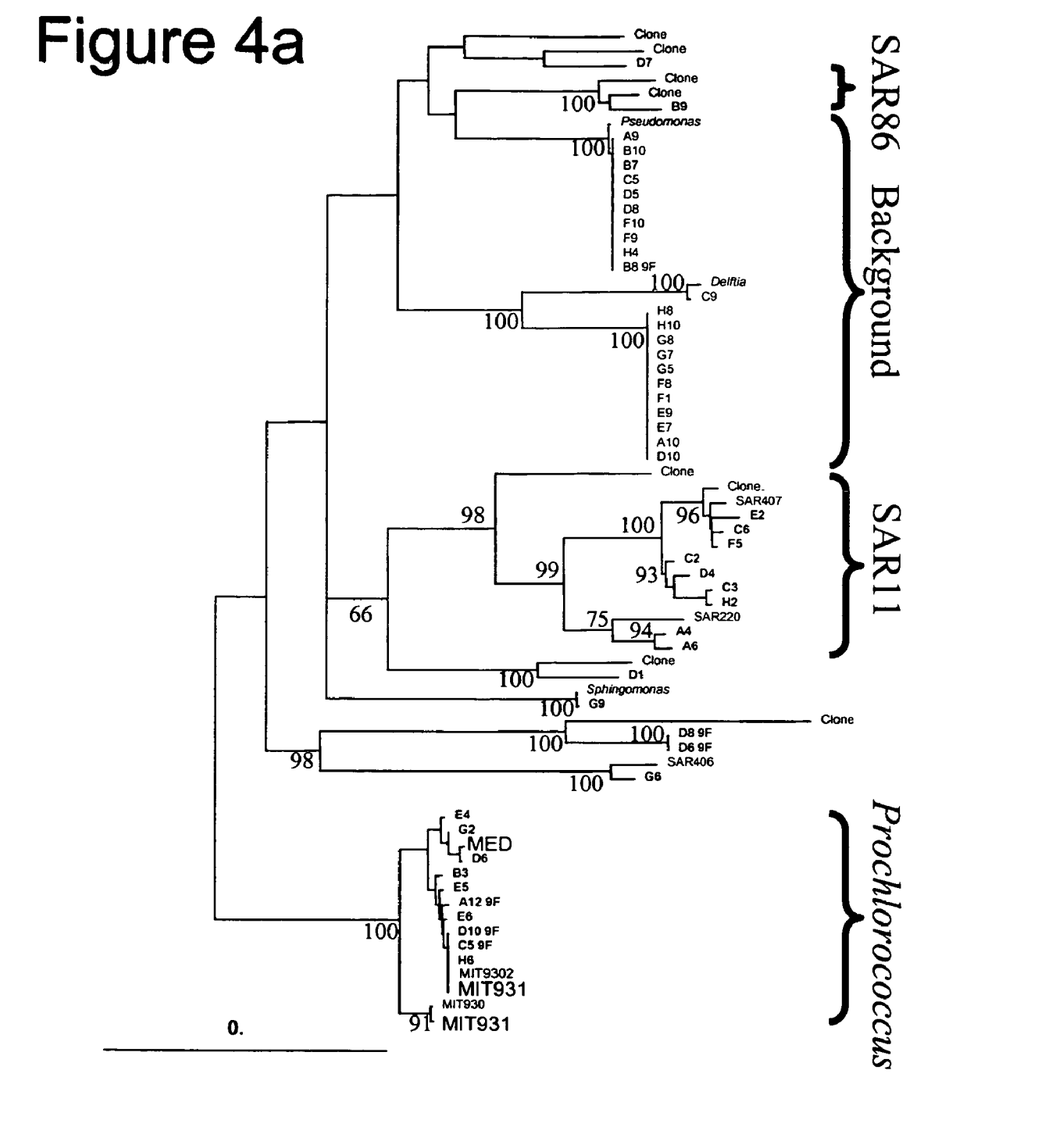
(FIG. 4A) The phylogeny tree of plones based on the 16S rRNA sequence.
Figure 4B:
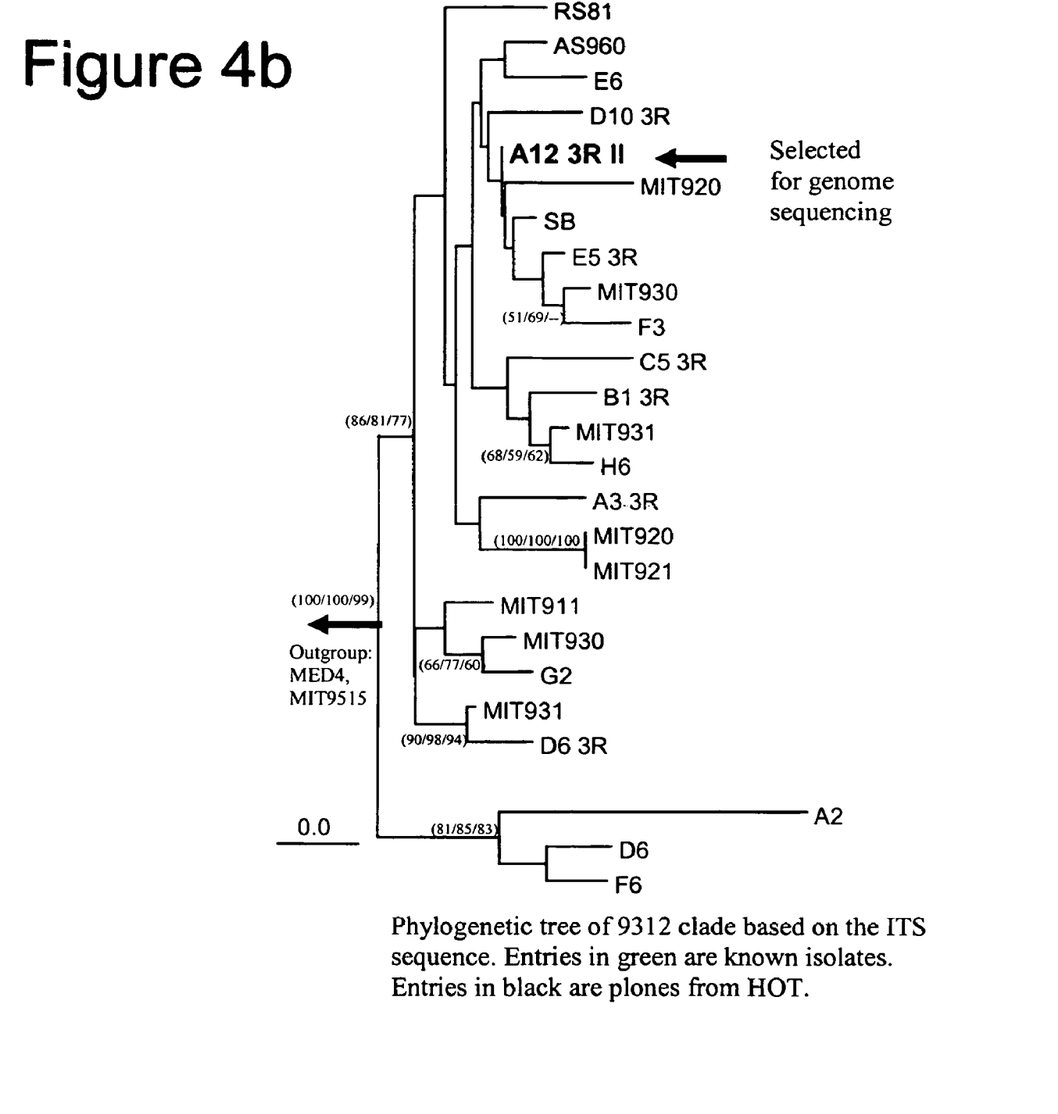
(FIG. 4B) The detailed phylogenetic structure of *Prochlorococcus* plones based on the ITS sequence.

Amplification from Hawaii Ocean Time-series samples (HOT). Using cells frozen in DMSO collected at the HOT station, we successfully ploned single cells from a variety of marine microorganism. The identity of cells was determined by 16S rRNA sequencing (FIG. 3a). The presence of only one cell in each reaction was verified by analysis of the sequencing trace file for a contaminating sequence. Plones originating from SAR11, SAR86 and *Prochlorococcus* were all detected in this samples. Additionally, contaminating sequences were found in wells containing no cell. We also sequenced the interegenic spacer region (ITS) from plones affiliated to *Prochlorococcus* to achieve higher resolution of closely related ecotypes (FIG. 3b). All *Prochlorococcus* plones were affiliated to the "9312"-clade. Plone "A12 3R II" is related to the most abundant microcluster. Based on this analysis, we selected plone "A12 3R II" for genome sequencing.

EXAMPLE 4

Real-time ultra-low background isothermal amplification. Since no current method is available to determine the level of background amplification, we developed an ultra-sensitive and sequence non-specific detection system by monitoring the dynamics of isothermal amplification in real time with SYBR Green I (Hafner et al. 2001). We found that MDA, like rolling-circle amplification (Lizardi et al. 1998), has an exponential growth stage, and that the time it takes for an amplification to reach its 50% of saturated level (t50) is a good summary statistic to capture the underlying amplification dynamics: there is a log-linear relationship between t50 and the amount of DNA templates (FIGS. 1A, 1B), thus providing a way to estimate background levels. Specifically, we calculated the background by comparing amplification curves from a DNA dilution series with known concentrations. In an amplification system with little background, amplification curves for templates of different concentrations are well separated (FIG. 1C). In contrast, in the presence of background DNA contamination, amplification curves for templates with low concentrations are compressed because template-dependent amplification is masked by background amplification (FIG. 1D). We performed logistic regression on the t50 values of the well separated curves, and calculated the background based on the best-fit line.[1] For example, the level of background amplification for the reactions in FIG. 1c is approximately 1.2 fg, which is about 150-fold lower than those in FIG. 1D (~180 fg).

[1] In order to calculate background amplification, logistical regression was performed between the amounts of amplification templates and the corresponding t50 values, and a best linear-fit line was determined. Based on the linear-fit line, the t50 value for the no-template control can be converted to DNA amount, which is the level of background contamination.

We sought to identify the sources of background amplification using such real-time monitoring. To distinguish endogenous background amplification due to primer-primer interaction from exogenous DNA contaminations, we designed a partially degenerate primer, R6 (a random hexameric sequence of A and G). Because there is no base-pairing potential between any two primer molecules, the amplification system with R6 is expected to have "zero-background" in the absence of exogenous contamination, which was observed experimentally. Using the R6 system as reference, we were able to identify common sources of exogenous DNA contamination, and hence to develop a strict sample handling and experimental procedure that reliably reduces endogenous DNA contamination to below ~$10^{-4}$ femtograms/reaction—10,000 times lower than a single copy of the *E. coli* genome. Using such a protocol, we investigated whether N6 and other partially degenerate primers are suitable for single-cell whole genome amplification. The doubling time, which is defined as the amount of time it takes to generate twice amount of DNA, for amplifications primed by seven degenerate short (6 to 9-mer) oligonucleotide were determined experimentally (Table 2). We were also able to estimate the endogenous background of these primers based on the "zero background" amplification system established with R6 primer. Although the three primers, 12M7, M6 and R6, have no potential for primer-primer interaction, they were excluded as good candidates for whole genome amplification because preliminary analysis revealed that they led to poor genome coverage (data not shown). For D6, H6 and W6 primers, only A:T base pairs can form, so we expected to see weaker primer-primer interaction compared with the totally degenerate N6 primer. Although G and C seem likely to be equivalent in priming, H6 has a surprisingly long doubling time compared with D6, which was confirmed by multiple experiments with different batches of primers. D6 has a shortest doubling time only second to N6, which on the other hand has an endogenous background amplification that is approximately 100,000 times higher (Table 2).

TABLE 2

Amplification dynamics and endogenous background of seven primers. To calculate doubling time, amplifications were performed on 10-fold dilution series of human genomic DNA from 3 ng to 3 fg, as well as on no-template controls. Logistic regressions were performed between the template concentrations and the time points that amplification curves reach 50% of their saturated intensities (t50). Pearson R indicates the goodness of fit between t50 and the amount of template (log-transformed). The endogenous background was determined with 8U/µl of Epicentre's phi29 DNA polymerase in quadruplicate.

| Primer+ | Doubling time (minutes) | Pearson R | Time required (hour)* | Endogenous background (g) |
|---|---|---|---|---|
| N6 | 5.9 | 0.983 | 2.6 | ~3 × $10^{-17}$ |
| D6 | 7.4 | 0.995 | 3.3 | ~2 × $10^{-23}$ |
| H6 | 18.8 | 0.994 | 8.3 | N.A. |
| M6 | 9.0 | 0.970 | 4.0 | <4 × $10^{-24}$ |
| R6 | 9.7 | 0.955 | 4.3 | <3 × $10^{-19}$ |
| W6 | 10.8 | 0.996 | 4.8 | ~1 × $10^{-22}$ |
| 12M7 | 63.1 | 0.971 | 28.0 | N.A. |

Notes:
+All primers have two phosphothioate bonds on the 3' end. N = (A/T/G/C); D = (A/G/T); H = (A/C/T); M = (A/C); R = (A/G); W = (A/C); I = deoxyinosine.
*The amount of time required to achieve $10^8$-fold amplification, calculated based on the doubling time.

We selected D6 and N6 as candidates for single-cell amplification. Other factors that affect the amplification dynamics, including primer concentration, enzyme vendor, and enzyme concentration, were also investigated. We found that, for primers with base-pairing potential, the level of endogenous background amplification depends on the amount of enzyme used. For example, the endogenous background amplification for the N6 primer can be reduced by ~18,000 fold using of 2U/ul (instead of the standard concentration 8U/ul) of phi29 DNA polymerase. However, even with the standard enzyme concentration used in the original MDA protocol, the endogenous background amplification of N6 is two orders of magnitude lower than the genome mass of a single E. coli cell, and thus unlikely to affect amplification coverage.

Therefore, to achieve successful amplification from a single cell, one should focus on minimizing exogenous DNA contamination instead of endogenous background amplification. We observed different levels of background amplification with enzymes from different vendors, and even among different batches from the same vendor, most likely because of different amounts of DNA contamination in commercial enzymes (Carroll et al. 1999; Corless et al. 2000). We found that an appropriate dosage of UV irradiation can suppress background contamination by approximately 1500-fold.

EXAMPLE 5

Single cell amplification. Having optimized a protocol to achieve ultra-low background, we next developed a method for single cell amplification. In developing this method we needed an experimental framework that would allow us to rapidly and reliably determine whether the amplification products were from single or multiple cells. For this, we used four strains of *E. coli* (NR56, NR57, NR58, NR59) that were constructed from a common strain EcNR1, a derivative of "wild-type" MG1655 containing a λ Red prophage integrated at the bio locus for use in recombineering[29]. Each strain has a particular gene or operon replaced by a chloramphenicol resistance (cat) marker; thus every strain can be uniquely identified by PCR with strain-specific markers. Like EcNR1, the four strains also share a common deletion at the bio locus compared with the MG1655 parent, which allows them to be distinguished from DNA contamination from other laboratory *E. coli* strains. In doing single cell amplification, we mixed cells from these four strains in a 1:1:1:1 ratio and made dilutions to the single-cell level. We then performed real-time isothermal amplification followed by PCR on the strain-specific markers. Assuming that the number of cells in each aliquot follows a Poisson distribution, and only one marker is amplified, the probability of having one cell in that particular aliquot is 88%, which is similar to the success rate of flow-sorted single cells(Gray et al. 1987). We thus considered amplicons showing only one band in the strain-specific PCR assay as single-cell amplicons (FIG. 2B), and selected them for further analysis.

EXAMPLE 6

Validation of real-time isothermal amplification from single cells. We evaluated the performance of real-time isothermal amplification from single *E. coli* cells in terms of amplification yield, specificity, amplification bias and genome coverage. DNA quantification with PicoGreen shows that the typical amplification yield from single *E. coli* cells is ~25 μg for the N6 primer and ~10 μg for the D6 primer in a 50 μl reaction, which is equivalent to an amplification magnitude of $10^9$~$10^{10}$. The amplification yield can be further improved by performing the second round of amplification by conventional MDA. We studied the other aspects of single-cell whole genome amplification with three experimental approaches. First we did quick screening of genome coverage by conducting real-time quantitative PCR with a set of eight markers that are evenly spaced across the *E. coli* genome, enabling us to optimize many parameters in our protocol in the initial stage of technology development. We then performed detailed characterization of single cell amplicons using Affymetrix *E. coli* Antisense Genome chips, as well as shotgun cloning and random sequencing.

We selected four single-cell amplicons (two from N6 primer and two from D6 primer amplifications, FIGS. 2A, 2B) for Affymetrix chip™ hybridization and calculated the ratios of normalized hybridization intensities for a total of 2231 non-overlapping windows (2-kb in size, covering 96.2% of the *E. coli* genome) across the chromosome between each amplicon and the unamplified genomic DNA control, MG1655. This "ratio profile" represents genome-wide relative locus enrichment. Comparison of the ratio profiles of unamplified genomic DNA from EcNR1 strain and MG1655 showed the bio deletion was easily detected by this method (FIG. 2C, left). We found the genetic signature (the bio locus deletion) was accurately preserved in the single cell amplicons (FIG. 2C). In addition, the strain-specific PCR indicates that the two N6 amplicons and one D6 amplicon were amplified from the NR57 strain, and the other D6 amplicon was from the NR56 strain. The strain-specific deletions were also detected based on the ratio profiles. These deletion signatures clearly show that, when the background is effective suppressed, the real-time isothermal amplification has high specificity to the target genome.

The genome coverage of a whole genome amplification method is usually estimated by performing PCR on a randomly selected set of markers (Cheung and Nelson 1996; Wells et al. 1999). Such a method only detects the presence or absence of a DNA region while ignoring the difference in copy number among different loci. It thereby tends to overestimate genome coverage, especially for the purpose of genome sequencing, because poorly amplified regions are difficult to capture by shotgun sequencing. Since we observed a 6.5-fold of increase of variability (in $\log_2$ space) across the genome in N6 amplicons compared with unamplified reference genomic DNA, and D6 amplicons exhibited even higher variability (FIG. 3a,b), estimating genome coverage by regular PCR is inappropriate. We were therefore interested in estimating the percentage of genome in the single cell amplicons that could be captured at a certain level of sequencing depth. We asked, for example, what is the percentage of the genome that can be sequenced at least once when the length of total sequencing reads is ten times of the target genome (a depth of 10×). We calibrated genome-wide ratio profiles with true copy numbers at the eight loci determined by real-time quantitative PCR, which are currently considered the gold standard for the measurement of copy number, then estimated the relative copy numbers at all loci across the genome, and finally calculated the genome coverage for the four single-cell amplicons at eight different levels of sequencing depth (Table 2). The N6 primer provides approximately twice amount of genome coverage than the D6 primer before the sequencing depth exceeds 50×. At the 10× level, both N6 amplicons have a near complete coverage of 97%, while, in contrast, the two D6 amplicons only cover 39% and 43% of the *E. coli* genome respectively. The low amplification coverage with the D6 primer is likely due to the fact that, theoretically speaking, the priming sites of D6 is 64-fold less frequent than that of N6. However, since we used UV-treated phi29 DNA polymerase for the D6 primer, one restricted-randomized hypothesis is that the low genome coverage is due to the loss of enzyme activity. To test this hypothesis, we performed additional amplifications with the D6 primer and un-treated enzyme, and selected one single-cell amplicon for Affymetrix chip hybridization. The ratio profile of this amplicons is similar to those of the amplicons with UV-treated enzyme suggesting that complete primer degeneracy is critical to achieve high genome coverage.

We next investigated whether some genomic regions are poorly amplified in a consistent manner, since, if such regions exist, they become the blind spots for genome sequencing regardless how many cells are sampled. Comparison of the ratio profiles between the two N6 amplicons shows little level of correlation (R=0.11). The two D6 amplicons have a modest level of correlation (R=0.45), but both the chromosome-wide profiles and the scatter plot suggest that the correlation is mostly explained by regions that are amplified better than the genome average level instead of poorly amplified regions. To confirm this hypothesis, we excluded regions that are overrepresented compared with the genome average level (log-transformed copy number ratio>0, comprising 48.7% of the genome) from the analysis of correlation, and found that the correlation coefficient between the two D6 amplicons dropped to 0.146; in contrast, when only overrepresented were considered, the correlation coefficiency rose to 0.65. Therefore, poorly amplified regions are more likely to occur at random locations. The poor correlation of ratio profiles between independent amplifications suggests that one could improve the coverage of genome sequencing by combining the sequencing reads from two or more single cell amplicons without increasing sequencing depth. In this strategy, preliminary sequencing or other genetic analyses (i.e., genotyping, species-specific PCR, etc.) can be performed to select amplicons from the same type of cells for sequencing, and then these sequences can be combined for assembly. The improvement of genome coverage is significant with the N6 primer. For example, a 10× sequencing depth is required to achieve 97% of genome coverage with one N6 amplicon. However, when two N6 single-cell amplicons are combined, a 2× sequencing depth for each amplicon (the total depth is 4×) can produce the same coverage, which is equivalent to the reduction of sequencing cost by 2.5-fold.

We finally performed shotgun cloning library construction and random sequencing in order to characterize the single-cell amplicons in an unbiased manner. To sample the best- and worst-case scenarios, we selected a N6 amplicon that has lowest inter-locus variation and a D6 amplicon with highest variation to construct shotgun libraries. In addition, two amplicons from the no-template controls, one for the N6 primer and the other for D6, were also included, so that we could further investigate the source of background amplification. For the two amplicons amplified from single *E. coli* cells, all clones that were successfully sequenced were mapped to the *E. coli* genomic sequence. No sequence from other organisms was discovered; nor did we observe any spurious amplification. There were, though, 6 mosaic sequences out of the 65 clones (9%) we sequenced. One mosaic sequence is composed of fragments that were mapped to three parts of the genome, with the middle fragment in the inverted orientation (Supplementary Figure S6). For the other five mosaic sequences, each has two fragments that are mapped to the genome in the same orientation. We hypothesized that these mosaic sequences could originate template switching during DNA synthesis (Murthy et al. 1998). This is important to establish since it has implications for the level of challenge of assembling the genome from single cell shotgun sequencing. We therefore designed PCR primers located in different fragments of one mosaic sequence. PCR result showed that the products from the single cell amplicon are exactly the same as those expected from the intact *E. coli* genome, indicating that the mosaic sequences do not exist in the single cell amplicons.

We have successfully suppressed background amplification to sub-femtogram levels in order to achieve WGA from single cells. Nevertheless, we still found amplification products in no-template controls, although amplification curves clearly show that such amplifications occur long after template-directed amplification (FIG. 2A). Of a total of 36 clones sequenced from the N6 no-template amplification, 29 clones do not have any match to the NCBI nr database, seven clones (19%) are known sequences: six were mapped to the *Micrococcus luteus* cryptic MLU1 plasmid, and one to the *Ralstonia solanacearum* GMI1000 megaplasmid. This suggests that there is a trace amount of DNA contamination in the commercial kit (the Molecular Staging's Repli-G kit). In contrast, three of 45 (6.7%) clones from the D6+UV no-template amplification were mapped to the human genome, while the remaining 42 clones have no match to any known sequence. The contamination of human DNA sequences was likely to be introduced in experimental handling. This again indicates the importance of a set of very strict sample handling and experimental procedures to minimize exogenous DNA contamination.

EXAMPLE 7

Ultra-low background real-time isothermal amplification. We developed a strict sample handling and experimental procedure, which we found is essential to achieve sub-femtogram levels of background. All experiments were conducted in an AirClean 1000 PCR hood (AirClean System, NC) with a dedicated set of pipettes. Unopened pipette tips were used for every experiment. Tubes, tube caps and all reagents, except for the primers, dNTPs, SYBR Green I and polymerases, are treated with UV for 5~10 minutes in a Stratalinker (Stratagene, CA, model # 1800). Primers and SYBR Green I were diluted with UV-treated RT-PCR grade water (Ambion, TX). We perform isothermal amplifications essentially as described by Dean et al. (Dean et al. 2002), except that SYBR Green I (Molecular Probes, OR) was added to the reaction to a final concentration of 0.1×, and the reactions were carried out in a real-time PCR thermocycler (Opticon 2, M J Research, MA) at 30° C. Fluorescent intensities were collected via the SYBR Green I channel every 6 or 15 minutes. The Repli-g kit (Molecular Staging, CT) and GenomiPhi kit (Amersham, NJ) were used for single-cell amplifications with the N6 primer. Home made reagents and RepliPHI phi29 DNA polymerase (Epicentre, WI) were used for amplification with other primers, all of which were purchased from IDT (IL). Since Epicentre's enzyme unit definition is different from other vendors, the final concentration of phi29 DNA polymerase in our protocol is 8U/μl. DNA dilution series were prepared with human genomic DNA-G147A (Promega, Wis.). We did not include yeast pyrophosphatase in our amplification mix as it could have been a source of additional DNA contamination. We UV-treated the phi29 DNA polymerase in inverted strip-tube caps placed on top of a chilled 96-well PCR cooler (Eppendorf, German) filled with water to avoid sample heating. The StrataLinker and a micro-centrifuge are placed right next to the PCR hood to reduce the risk of contamination. Tubes, reagents were covered when transferred between the PCR hood and the StrataLinker. Real-time isothermal amplification data were exported by the Opticon2 program, and analyzed by a Perl script.

REFERENCES

Beaumont, M. A. and B. Rannala. 2004. The Baysian Revolution in Genetics. *Nature Review Genetics* 5: 251-261.

Carroll, N. M., P. Adamson, and N. Okhravi. 1999. Elimination of bacterial DNA from Taq DNA polymerases by restriction endonuclease digestion. *J Clin Microbiol* 37: 3402-3404.

Cheung, V. G. and S. F. Nelson. 1996. Whole genome amplification using a degenerate oligonucleotide primer allows hundreds of genotypes to be performed on less than one nanogram of genomic DNA. *Proc Natl Acad Sci USA* 93: 14676-14679.

Corless, C. E., M. Guiver, R. Borrow, V. Edwards-Jones, E. B. Kaczmarski, and A. J. Fox. 2000. Contamination and sensitivity issues with a real-time universal 16S rRNA PCR. *J Clin Microbiol* 38: 1747-1752.

Czerniak, B., L. Li; V. Chaturvedi, J. Y. Ro, D. A. Johnston, S. Hodges, and W. F. Benedict. 2000. Genetic modeling of human urinary bladder carcinogenesis. *Genes Chromosomes Cancer* 27: 392-402.

Dean, F. B., S. Hosono, L. Fang, X. Wu, A. F. Faruqi, P. Bray-Ward, Z. Sun, Q. Zong, Y. Du, J. Du, M. Driscoll, W. Song, S. F. Kingsmore, M. Egholm, and R. S. Lasken. 2002. Comprehensive human genome amplification using multiple displacement amplification. *Proc Natl Acad Sci USA* 99: 5261-5266.

Dietmaier, W., A. Hartmann, S. Wallinger, E. Heinmoller, T. Kerner, E. Endl, K. W. Jauch, F. Hofstadter, and J. Ruschoff. 1999. Multiple mutation analyses in single tumor cells with improved whole genome amplification. *Am J Pathol* 154: 83-95.

Douglas, J. A., M. Boehnke, E. Gillanders, J. M. Trent, and S. B. Gruber. 2001. Experimentally-derived haplotypes substantially increase the efficiency of linkage disequilibrium studies. *Nat Genet* 28: 361-364.

Falkowski, P. G. and C. de Vargas. 2004. Genomics and evolution. Shotgun sequencing in the sea: a blast from the past? *Science* 304: 58-60.

Gray, J. W., P. N. Dean, J. C. Fuscoe, D. C. Peters, B. J. Trask, G. J. van den Engh, and M. A. Van Dilla. 1987. High-speed chromosome sorting. *Science* 238: 323-329.

Hafner, G. J., I. C. Yang, L. C. Wolter, M. R. Stafford, and P. M. Giffard. 2001. Isothermal amplification and multimerization of DNA by Bst DNA polymerase. *Biotechniques* 30: 852-856, 858, 860 passim.

Handyside, A. H., M. D. Robinson, R. J. Simpson, M. B. Omar, M. A. Shaw, J. G. Grudzinskas, and A. Rutherford. 2004. Isothermal whole genome amplification from single and small numbers of cells: a new era for preimplantation genetic diagnosis of inherited disease. *Mol Hum Reprod* 10: 767-772.

Hellani, A., S. Coskun, M. Benkhalifa, A. Thakhi, N. Sakati, A. Al-Odaib, and P. Ozand. 2004. Multiple displacement amplification on single cell and possible PGD applications. *Mol Hum Reprod* 10: 847-852.

Hosono, S., A. F. Faruqi, F. B. Dean, Y. Du, Z. Sun, X. Wu, J. Du, S. F. Kingsmore, M. Egholm, and R. S. Lasken. 2003. Unbiased whole-genome amplification directly from clinical samples. *Genome Res* 13: 954-964.

Klein, C. A., O. Schmidt-Kittler, J. A. Schardt, K. Pantel, M. R. Speicher, and G. Riethmuller. 1999. Comparative genomic hybridization, loss of heterozygosity, and DNA sequence analysis of single cells. *Proc Natl Acad Sci USA* 96: 4494-4499.

Lage, J. M., J. H. Leamon, T. Pejovic, S. Hamann, M. Lacey, D. Dillon, R. Segraves, B. Vossbrinck, A. Gonzalez, D. Pinkel, D. G. Albertson, J. Costa, and P. M. Lizardi. 2003. Whole genome analysis of genetic alterations in small DNA samples using hyperbranched strand displacement amplification and array-CGH. *Genome Res* 13: 294-307.

Lasken, R. S. and M. Egholm. 2003. Whole genome amplification: abundant supplies of DNA from precious samples or clinical specimens. *Trends Biotechnol* 21: 531-535.

Lizardi, P. M., X. Huang, Z. Zhu, P. Bray-Ward, D. C. Thomas, and D. C. Ward. 1998. Mutation detection and single-molecule counting using isothermal rolling-circle amplification. *Nat Genet* 19: 225-232.

Lovatt, A. 2002. Applications of quantitative PCR in the biosafety and genetic stability assessment of biotechnology products. *J Biotechnol* 82: 279-300.

Mitra, R. D., V. L. Butty, J. Shendure, B. R. Williams, D. E. Housman, and G. M. Church. 2003. Digital genotyping and haplotyping with polymerase colonies. *Proc Natl Acad Sci USA* 100: 5926-5931.

Moreira, D. and P. Lopez-Garcia. 2002. The molecular ecology of microbial eukaryotes unveils a hidden world. *Trends Microbiol* 10: 31-38.

Murthy, V., W. J. Meijer, L. Blanco, and M. Salas. 1998. DNA polymerase template switching at specific sites on the phi29 genome causes the in vivo accumulation of subgenomic phi29 DNA molecules. *Mol Microbiol* 29: 787-798.

Nelson, J. R., Y. C. Cai, T. L. Giesler, J. W. Farchaus, S. T. Sundaram, M. Ortiz-Rivera, L. P. Hosta, P. L. Hewitt, J. A. Mamone, C. Palaniappan, and C. W. Fuller. 2002. TempliPhi, phi29 DNA polymerase based rolling circle amplification of templates for DNA sequencing. *Biotechniques* Suppl: 44-47.

Paez, J. G., M. Lin, R. Beroukhim, J. C. Lee, X. Zhao, D. J. Richter, S. Gabriel, P. Herman, H. Sasaki, D. Altshuler, C. Li, M. Meyerson, and W. R. Sellers. 2004. Genome coverage and sequence fidelity of phi29 polymerase-based multiple strand displacement whole genome amplification. *Nucleic Acids Res* 32: e71.

Shendure, J., R. D. Mitra, C. Varma, and G. M. Church. 2004. Advanced sequencing technologies: methods and goals. *Nature Review Genetics* 5: 335-344.

Sorensen, K. J., K. Turteltaub, G. Vrankovich, J. Williams, and A. T. Christian. 2004. Whole-genome amplification of DNA from residual cells left by incidental contact. *Anal Biochem* 324: 312-314.

Telenius, H., N. P. Carter, C. E. Bebb, M. Nordenskjold, B. A. Ponder, and A. Tunnacliffe. 1992. Degenerate oligonucleotide-primed PCR: general amplification of target DNA by a single degenerate primer. *Genomics* 13: 718-725.

VanDevanter, D. R., N. M. Choongkittaworn, K. A. Dyer, J. Aten, P. Otto, C. Behler, E. M. Bryant, and P. S. Rabinovitch. 1994. Pure chromosome-specific PCR libraries from single sorted chromosomes. *Proc Natl Acad Sci USA* 91: 5858-5862.

Venter, J. C., K. Remington, J. F. Heidelberg, A. L. Halpern, D. Rusch, J. A. Eisen, D. Wu, I. Paulsen, K. E. Nelson, W.

Nelson, D. E. Fouts, S. Levy, A. H. Knap, M. W. Lomas, K. Nealson, O. White, J. Peterson, J. Hoffinan, R. Parsons, H. Baden-Tillson, C. Pfannkoch, Y. H. Rogers, and H. O. Smith. 2004. Environmental genome shotgun sequencing of the Sargasso Sea. *Science* 304: 66-74.

Wells, D., J. K. Sherlock, A. H. Handyside, and J. D. Delhanty. 1999. Detailed chromosomal and molecular genetic analysis of single cells by whole genome amplification and comparative genomic hybridisation. *Nucleic Acids Res* 27: 1214-1218.

Yu, D., H. M. Ellis, E. C. Lee, N. A. Jenkins, N. G. Copeland, and D. L. Court. 2000. An efficient recombination system for chromosome engineering in *Escherichia coli. Proc Natl Acad Sci USA* 97: 5978-5983.

Zhang, L., X. Cui, K. Schmitt, R. Hubert, W. Navidi, and N. Arnheim. 1992. Whole genome amplification from a single cell: implications for genetic analysis. *Proc Natl Acad Sci USA* 89: 5847-5851.

What is claimed is:

1. A method of nucleic acid amplification, comprising:
   exposing a sample of polymerase to ultraviolet light for a sufficient time to reduce nucleic acid contamination of said polymerase to produce an exposed sample of polymerase; and
   amplifying a reaction mixture comprising a nucleic acid template, the exposed sample of polymerase, and one or more restricted-randomized oligonucleotide primers,
   wherein the amplifying is real time amplification performed a plurality of times with a plurality of known amounts of a nucleic acid template and wherein data is obtained from the real time amplification and logistical regression analysis is performed on the data to calculate an amount of background nucleic acid contamination.

2. A method of nucleic acid amplification, comprising:
   amplifying a nucleic acid template in a reaction mixture comprising:
   one or more restricted-randomized oligonucleotide primers, wherein the one or more restricted-randomized primers do not comprise random hexamers ($N_6$, wherein N=A, C, G, or T),
   a template-dependent polymerase, and
   mononucleotide triphosphates,
   wherein the amplifying is real time amplification performed under conditions permitting hybridization of the primers to the template and wherein data is obtained from the real time amplification and logistical regression analysis is performed on the data.

3. The method of claim 1 wherein the concentration of nucleic acid template in the reaction mixture is at least 100-fold greater than the concentration of nucleic acid contamination.

4. The method of claim 2 wherein the one or more restricted-randomized oligonucleotide primers are selected from the group consisting of:
   $B_6$ (wherein B=not A=C+G+T),
   $D_6$ (wherein D=not C=A+G+T),
   $H_6$ (wherein H=not G=A+C+T),
   $V_6$ (wherein V=not T=A+G+C),
   $M_6$ (wherein M=A+C),
   $W_6$ (wherein W=A+T),
   $Y_6$ (wherein Y=T+C),
   $R_6$ (wherein R=A+G),
   $I_3D_4$ (wherein I=inosine, and wherein D=not C),
   $I_2M_7$, (wherein I=inosine and M=A+C),
   $M_7$ (wherein M=A+C), and combinations thereof.

5. The method of claim 2 wherein the restricted-randomized primers comprise $K_6$ (wherein K=G+T/U).

6. The method of claim 2 wherein the restricted-randomized primers are hexamers, heptamers, or combinations thereof.

7. The method of claim 2 wherein the restricted-randomized primers are hexamers.

8. The method of claim 2 wherein the restricted-randomized primers are heptamers.

9. The method of claim 1 wherein the step of exposing comprises applying between 100 and 500 mJ of UV to 5-10 ul of polymerase.

10. The method of claim 1 wherein the step of amplifying employs real-time isothermal amplification.

11. The method of claim 2 wherein the restricted-randomized oligonucleotide primer is $R_6$.

12. The method of claim 2 wherein the restricted-randomized oligonucleotide primer is $M_6$.

13. The method of claim 1 wherein the step of amplifying employs a restricted-randomized oligonucleotide primer selected from the group consisting of $R_6$ or $M_6$.

14. The method of claim 1 wherein the nucleic acid contamination is reduced 100-fold by said step of exposing.

15. The method of claim 1 wherein the nucleic acid contamination is reduced 1000-fold by said step of exposing.

16. The method of claim 1 wherein the nucleic acid contamination is reduced 1,500-fold by said step of exposing.

17. The method of claim 1 wherein the nucleic acid contamination is reduced by said step of exposing to less than $3 \times 10^{-14}$ g in the exposed sample of polymerase.

18. The method of claim 1 wherein the nucleic acid contamination is reduced by said step of exposing to less than $3 \times 10^{-17}$ g in the exposed sample of polymerase.

19. The method of claim 1 wherein the nucleic acid contamination is reduced by said step of exposing to less than $3 \times 10^{-19}$ g in the exposed sample of polymerase.

20. The method of claim 1 wherein the nucleic acid contamination is reduced by said step of exposing to less than $3 \times 10^{-21}$ g in the exposed sample of polymerase.

21. The method of claim 1 wherein the nucleic acid contamination is reduced by said step of exposing to less than $3 \times 10^{-23}$ g in the exposed sample of polymerase.

22. The method of claim 2 wherein said step of amplifying is performed a plurality of times with a plurality of known amounts of a nucleic acid template.

23. The method of claim 2 wherein the logistical regression analysis is used to calculate an amount of background nucleic acid contamination.

24. The method of claim 23 wherein the amount of background nucleic acid contamination calculated is used to determine a sufficient amount of time to expose a sample of polymerase to ultraviolet light.

25. The method of claim 1 wherein the nucleic acid template is present at a concentration of less than 1 ng in the reaction mixture.

26. The method of claim 1 wherein the nucleic acid template is present at a concentration of less than 1 pg in the reaction mixture.

27. The method of claim 1 wherein the nucleic acid template is present at a concentration of less than 1 fg in the reaction mixture.

28. The method of claim 1 wherein the template is a single chromosome obtained by flow-sorting.

29. The method of claim 1 wherein the template is a single chromosome obtained by dilution.

30. The method of claim 1 wherein the template is a chromosome of a single cell.

31. The method of claim 1 wherein the one or more restricted-randomized oligonucleotide primers are selected from the group consisting of:
$B_6$ (wherein B=not A=C+G+T),
$D_6$ (wherein D=not C=A+G+T),
$H_6$ (wherein H=not G=A+C+T),
$V_6$ (wherein V=not T=A+G+C),
$M_6$ (wherein M=A+C),
$W_6$ (wherein W=A+T),
$Y_6$ (wherein Y=T+C),
$R_6$ (wherein R=A+G),
$I_3D_4$ (wherein I=inosine, and wherein D=not C),
$I_2M_7$, (wherein I=inosine and M=A+C),
$M_7$ (wherein M=A+C), and combinations thereof.

32. The method of claim 1 wherein the restricted-randomized primers comprise $K_6$ (wherein K=G+T/U).

33. The method of claim 1 wherein the restricted-randomized primers are hexamers, heptamers, or combinations thereof.

34. The method of claim 1 wherein the restricted-randomized primers are hexamers.

35. The method of claim 1 wherein the restricted-randomized primers are heptamers.

36. The method of claim 1 wherein the restricted-randomized oligonucleotide primer is $R_6$.

37. The method of claim 1 wherein the restricted-randomized oligonucleotide primer is $M_6$.

38. The method of claim 2 wherein the step of amplifying employs a restricted-randomized oligonucleotide primer selected from the group consisting of $R_6$ or $M_6$.

39. The method of claim 1 wherein the amount of background nucleic acid contamination calculated is used to determine a sufficient amount of time to expose a sample of polymerase to ultraviolet light.

40. The method of claim 2 wherein the template is a single chromosome obtained by flow-sorting.

41. The method of claim 2 wherein the template is a single chromosome obtained by dilution.

42. The method of claim 2 wherein the template is a chromosome of a single cell.

* * * * *